United States Patent
Zhao et al.

(10) Patent No.: US 9,426,985 B2
(45) Date of Patent: Aug. 30, 2016

(54) COMPOSITIONS AND METHODS TO MODULATE THE RATE OF EBIS PRODUCTION FROM DITHIOCARBAMATE FUNGICIDES

(71) Applicant: Dow Agrosciences LLC, Indianapolis, IN (US)

(72) Inventors: Min Zhao, Midland, MI (US); Lei Liu, Carmel, IN (US); J. Todd Mathieson, Brownsburg, IN (US); Robert J. Ehr, Indianapolis, IN (US); Maria E. Rodriguez Rosas, Carmel, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 14/141,741

(22) Filed: Dec. 27, 2013

(65) Prior Publication Data

US 2014/0186451 A1    Jul. 3, 2014

Related U.S. Application Data

(60) Provisional application No. 61/747,664, filed on Dec. 31, 2012.

(51) Int. Cl.
*A01N 25/26*    (2006.01)
*A01N 47/14*    (2006.01)

(52) U.S. Cl.
CPC .............. *A01N 25/26* (2013.01); *A01N 47/14* (2013.01)

(58) Field of Classification Search
None
See application file for complete search history.

(56) References Cited

U.S. PATENT DOCUMENTS

| | | |
|---|---|---|
| 2,751,416 A | 6/1956 | Nadier |
| 3,379,610 A | 4/1968 | Channing |
| 3,589,674 A | 6/1971 | Jones |
| 3,814,803 A | 6/1974 | Eckfeldt |
| 3,869,486 A | 3/1975 | Van Den Boogaart |
| 4,217,293 A | 8/1980 | Adams, Jr. |
| 4,344,890 A | 8/1982 | Adams |
| 5,001,150 A | 3/1991 | Yap |
| 5,021,594 A | 6/1991 | Nouws |
| 5,922,337 A | 7/1999 | Hoy |
| 6,004,570 A | 12/1999 | Kostansek |
| 6,036,971 A * | 3/2000 | Kimoto et al. ............... 424/419 |
| 6,200,586 B1 * | 3/2001 | Lambie et al. ............... 424/417 |

(Continued)

FOREIGN PATENT DOCUMENTS

| | | |
|---|---|---|
| CA | 2093737 | 11/1993 |
| CH | 416 211 | 6/1966 |
| CH | 482 408 | 12/1969 |

(Continued)

OTHER PUBLICATIONS

"Mancozeb", Extension Technology Network, Publication date Sep. 1993, http://pmep.cce.cornell.edu/profiles/extonet/haloxyfop-methylparathion/mancozeb-ext.html (accessed Feb. 22, 2015).*

(Continued)

*Primary Examiner* — Bethany Barham
*Assistant Examiner* — Barbara Frazier
(74) *Attorney, Agent, or Firm* — C. W. Arnett; Faegre Baker Daniels LLP

(57) ABSTRACT

New compositions and methods are described for modulating the rate of conversion of ethylene bisdithiocarbamate fungicides, such as mancozeb, into ethylene bis-isothiocyanate sulfide (EBIS).

14 Claims, 1 Drawing Sheet

(56) References Cited

U.S. PATENT DOCUMENTS

| | | |
|---|---|---|
| 2008/0085935 A1 | 4/2008 | Pearson |
| 2011/0086761 A1 | 4/2011 | Pearson |

FOREIGN PATENT DOCUMENTS

| | | |
|---|---|---|
| CN | 101554161 A | 10/2009 |
| CN | 102217620 A | 10/2011 |
| DE | 12 34 087 | 2/1967 |
| DE | 19 17 458 | 10/1969 |
| EP | 0 460 612 | 12/1991 |
| EP | 0 568 378 | 11/1993 |
| GB | 1427243 | 3/1976 |
| JP | 47-034927 B | 9/1972 |
| JP | 48-007765 B | 3/1973 |
| JP | 52-117422 A | 10/1977 |
| JP | 52-117424 A | 10/1977 |
| JP | 53-014614 B | 5/1978 |
| JP | S54151123 | 11/1979 |
| JP | 56-133202 A | 10/1981 |
| JP | S56133202 | 10/1981 |
| JP | 2002114603 | 4/2002 |
| JP | 2006-157212 | 6/2006 |
| JP | 2007-109207 | 4/2007 |
| PL | 187964 | 11/2004 |
| WO | 9723486 | 7/1997 |

OTHER PUBLICATIONS

International Searching Authority, International Search Report and Written Opinion for PCT/US2013/077566, dated Apr. 23, 2014, 8 pages.

HCAPLUS Abstract 1962:485516 (1962).

Brenchley, W.E., "The essential nature of certain minor elements for plant nutrition," The Botanical Review, vol. II, No. 4, pp. 173-196 (1936).

Wojcik, P., et al., "Effects of boron fertilization on conference pear tree vigor, nutrition, and fruit yield and storability," Plant and Soil, vol. 256, pp. 413-421 (2003).

Kumagai, H., Nakamoto, K, Nakamura, M., Hirose, S., Ichikawa, Y., Endo, J., Ikari, H. 1992. Degradation of Dithiocarbamate Fungicide Polycarbamate in Upland Soils. Biosciences, Biotechnology, and Biochemistry. 56 (5). 828-830.

Fishbein, L. 1976. Environmental health aspects of fungicides. I. Dithiocarbamates. Journal of Toxicology and Environmental Health. 1(5). 713-735.

Engst, R., Schnaak, W. Residues of dithiocarbamate fungicides and their metabolites on plant foods. 1974. Srpinger-Verlag New York Inc. 45-64.

Lentza-Rizos, Ch. Ethylenethiourea (ETU) in relation to use of ethylenebisdithiocarbamate (EBDC) fungicides. 1990. Springer-Verlag New York, Inc. 1-32.

Notice of Reasons for Rejection dated May 27, 2014 (English-language translation), Japanese Patent Application No. 2009-531453, 2 pages.

Decision of Rejection dated Nov. 5, 2013 (English-language translation), Japanese Patent Application No. 2009-531453, 3 pages.

Notice of Reasons for Rejection dated Oct. 9, 2012 (English-language translation), Japanese Patent Application No. 2009-531453, 5 pages.

European Search Report, EP13867021.1, EPO, May 23, 2016.

\* cited by examiner

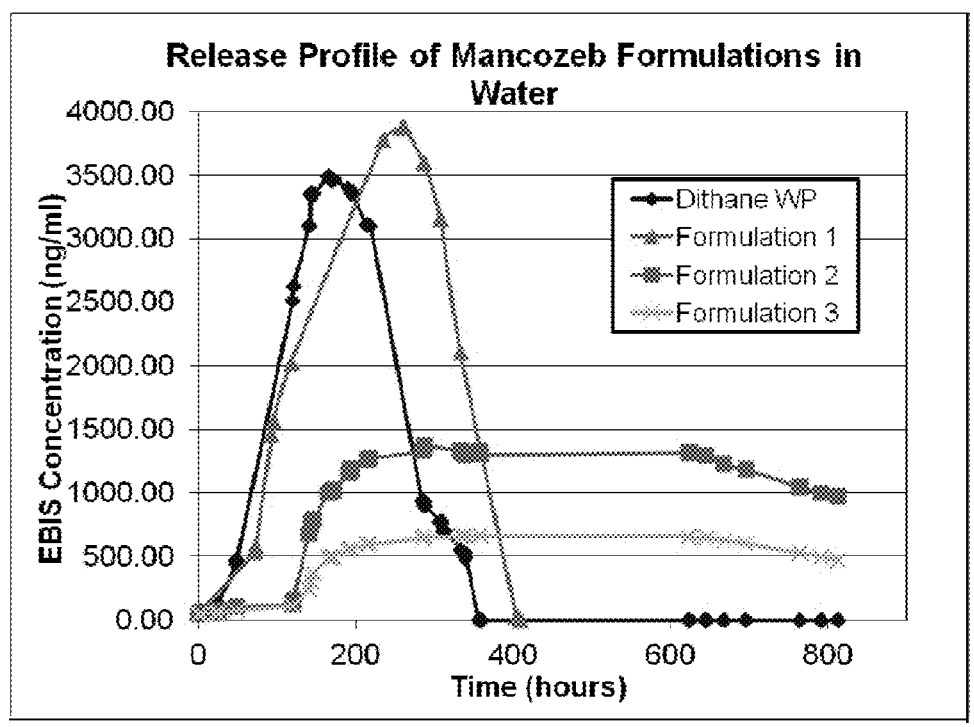

COMPOSITIONS AND METHODS TO MODULATE THE RATE OF EBIS PRODUCTION FROM DITHIOCARBAMATE FUNGICIDES

CROSS REFERENCE TO RELATED APPLICATIONS

This application claims the benefit of U.S. Provisional Patent Application Ser. No. 61/747,664, filed Dec. 31, 2012, which is hereby expressly incorporated by reference in its entirety.

FIELD

This disclosure relates to methods and compositions suitable for controlling fungal plant pathogens.

BACKGROUND AND SUMMARY

Ethylene bisdithiocarbamate (EBDC) fungicides, such as maneb and mancozeb, are important plant protection substances used for broad-spectrum disease control of more than 400 plant diseases in more than 70 crops (Ladovica, M., et. al. 2010. *Plant Disease* 94(9) 1076-1087. Mancozeb is especially important for controlling devastating and fast spreading diseases such as Late Blight of Potato caused by *Phytophthora infestans*, Apple scab caused by *Venturia inaequalis*, Downy mildew of grape caused by *Plasmopara viticola* and Sigatoka diseases of banana caused by various species of the genus, *Mycosphaerella*. Dithiocarbamate fungicides, especially mancozeb, are particularly useful for disease control because of their broad spectrum of activity, high tolerance by crop plants, and general usefulness for controlling fungal plant diseases resistant to certain fungicides that are active on only a single target site in the fungus.

Although EBDC fungicides are used widely, they have limitations due in part to the fact that many of them are in fact pre-fungicides and they do not exhibit significant antifungal activity until after they undergo conversion to a more fungicidal substance. For example, mancozeb is a pro-fungicide which, when exposed to water and oxygen, is rapidly converted to ethylene bisisthiocyanate sulfide (EBIS). Both oxygen and water are required in order to produce EBIS from EBDC fungicide. Sufficient oxygen for EBIS generation is present in the atmosphere. Sufficient water for EBIS generation can be provided by moisture in the forms of rain, dew, fog, mist, irrigation or periods of high humidity that may or may not be accompanied by free moisture. Once an EBDC fungicide has been applied to plants, EBIS generation is not limited by insufficient oxygen. However, the conversion of EBDC to EBIS may be limited by insufficient moisture. "Conversion" as used herein unless noted otherwise, means the formation of EBIS from EBDC by the reaction of EBDC with oxygen and water. While EBIS is the primary fungicidal toxicant produced from mancozeb, it remains present on the leaf surface at levels effective for disease control for only a short period of time, often with a half-life of less than 2 days. A study by Newsome (*J. Agric. Food Chem.* 1976(24), 999) reported that the degradation of mancozeb to EBIS reached peak levels about two days after application to tomato leaves.

The same general conditions leading to infection of plants by many fungal diseases also leads to the rapid generation and dissipation of fungicidal EBIS. Due to the relatively short period of their effectiveness under conditions conducive to plant disease, dithiocarbamates must often be re-applied at short intervals. Mancozeb also faces other practical use limitations. Previously, mancozeb was used in some European crops at rates as high as 2.8 kg of actual mancozeb per hectare. When mancozeb was re-registered in Europe, the maximum use rate was reduced to 1.6 kg per hectare. This regulation change has limited mancozeb's use on crops in Europe.

In order to improve the usefulness of dithiocarbamates for disease control, there is a need to increase the preventative effect of an individual application of the compound or to lengthen the time between applications, or both. Extensive modeling of mancozeb environmental fate in the phyllosphere has characterized the kinetics of EBIS generation from mancozeb on the leaf surface under a range of conditions conducive to fungal attack (Cryer, et. al. (*Computers and Electronics in Agriculture* (submitted for review/publication)). Cryer's model suggested that delaying the onset of the generation of EBIS from mancozeb or slowing its rate of release from mancozeb on the leaf surface would improve its disease control effectiveness. There appears to be little precedent in the published literature for controlling the actual conversion rate of a pro-pesticide into its active form on plant surfaces.

As reported herein, compositions that could modulate the reaction of mancozeb with water and oxygen to controllably release EBIS for an extended duration, may provide improvements such as 1) reducing the use rate of mancozeb necessary to control fungi, 2) extending the spray interval, 3) minimizing the degradation bi-product, i.e. ethylenethiourea (ETU).

Compositions and methods for modulating the rate of conversion of EBDC fungicides, such as mancozeb, into EBIS are disclosed herein. The described compositions suitable for providing improved disease control are comprised of an agriculturally effective amount of an EBDC fungicide, one or more EBIS-modulating polymers, one or more dispersants, and, optionally, other inert formulation ingredients.

In some exemplary embodiments, a fungicidal composition for modulating the conversion of an ethylene bisdithiocarbamate (EBDC) fungicide to ethylene bis-isothiocyanate sulfide (EBIS) is provided. The composition includes: an EBDC fungicide; an EBIS conversion-modulating polymer; and a dispersant. The EBDC fungicide is coated with the EBIS conversion-modulating polymer, such that the EBIS release half-life is increased by a factor of at least about 2 when compared to the uncoated EBDC fungicide.

In some exemplary embodiments of the fungicidal composition, the EBDC fungicide is at least one compound selected from the group consisting of: mancozeb, maneb, zineb and metiram. In a more particular embodiment, the EBDC fungicide is mancozeb.

In some exemplary embodiments of the fungicidal composition, the EBDC fungicide is in the form of solid particles. In a more particular embodiment, the EBDC fungicide is mancozeb.

In some exemplary embodiments of the fungicidal composition, the EBDC fungicide is distributed in a matrix of the EBIS conversion-modulating polymer. In a more particular embodiment, the EBDC fungicide is mancozeb.

In some exemplary embodiments of the fungicidal composition, the EBDC fungicide is in the form of crystals and/or solid particles and where the EBDC fungicides that are coated by the EBIS conversion-modulating polymer. In a more particular embodiment, the EBDC fungicide is mancozeb.

In some exemplary embodiments of the fungicidal composition, the EBDC fungicide produces ethylene bis-isothiocyanate sulfide (EBIS) when contacted with water and oxygen.

In some exemplary embodiments of the fungicidal composition, the EBIS conversion-modulating polymer provides a barrier to oxygen and/or water. In a more particular embodiment, the EBIS conversion-modulating polymer is at least one polymer selected from the group consisting of: a polyvinyl alcohol, a latex, a gelatin, a polyvinylpyrrolidone, a polyacrylate, a polyacrylamide, a polyvinylacetate, a polyvinylamine, a polyvinylsulfonate and mixtures and copolymers thereof. In a further more particular embodiment, the latex is selected from the group consisting of: standard or modified acrylic latex, standard or modified vinyl-acrylic latex, and styrene-acrylic latex. In another more particular embodiment, the polyvinyl alcohol is selected from partially hydrolyzed polyvinyl alcohols and co-polymers of partially hydrolyzed polyvinyl alcohols. An exemplary molecular weight range of the polyvinyl alcohol is from about 10,000 kDa to about 500,000 kDa and an exemplary degree of hydrolysis is from 60% to 99.9%. Another exemplary molecular weight range of the polyvinyl alcohol is from about 140,000 kDa to about 500,000 kDa and another exemplary degree of hydrolysis is from 87% to 99.9%.

In some exemplary embodiments of the fungicidal composition, the weight ratio of the EBIS conversion-modulating polymer to the EBDC fungicide in the composition is between about 1:200 to about 1:5.

In some exemplary embodiments of the fungicidal composition, the weight ratio of the EBIS conversion-modulating polymer to the EBDC fungicide is between 1:100 and 1:10.

In some exemplary embodiments of the fungicidal composition, the dispersant is at least one of the dispersant selected from the group consists of: sodium, calcium or ammonium lignosulfonate, alkyl naphthalene sulfonate condensate, ethylene oxide/propylene oxide block copolymer, tristyrylphenol ethoxylates styrene-acrylic copolymers, methylvinylether-maleic anhydride half ester copolymer, polyvinyl pyrrolidone, and a poly vinyl pyrrolidone copolymer.

In some exemplary embodiments of the fungicidal composition, the compound is in the form of a wettable powder.

In some exemplary embodiments of the fungicidal composition, the compound is in the form of a granule.

In some exemplary embodiments of the fungicidal composition, the compound is in the form of a water dispersible granule.

In some exemplary embodiments of the fungicidal composition, the compound is produced by a spray drying process.

In some exemplary embodiments, an aggregate solid particle is provided. The aggregate solid particle comprises an EBDC fungicide; a matrix or coating, wherein the matrix or the coating includes an EBIS conversion-modulating polymer, wherein the weight ratio of the EBIS conversion-modulating polymer to the EBDC fungicide is from about 1:200 to about 1:5, and wherein the EBIS conversion-modulating polymer is at least one polymer selected from the group consisting of: polyvinyl alcohol, latex, gelatin, polyvinylpyrrolidone, polyacrylate, polyacrylamide, polyvinylacetate, polyvinylamine, and polyvinylsulfonate; and a dispersant.

In some exemplary embodiments of the aggregarte solid particle, the EBDC fungicide is distributed in a matrix of the EBIS conversion-modulating polymer.

In some exemplary embodiments of the aggregarte solid particle, the EBDC fungicide is coated by the EBIS conversion-modulating polymer.

In some exemplary embodiments of the aggregarte solid particle, the particle is from about 1 to about 100 microns in size.

In some exemplary embodiments of the aggregarte solid particle, the EBDC fungicide is selected from the group consisting of: mancozeb, maneb, metiram, and zineb.

In some exemplary embodiments of the aggregarte solid particle, the latex is selected from the group consisting of: standard or modified acrylic latex, standard or modified vinyl-acrylic latex, and styrene-acrylic latex.

In some exemplary embodiments of the aggregarte solid particle, the polyvinyl alcohol is at least one polymer selected from the group consisting of: partially hydrolyzed polyvinyl alcohol, and a co-polymer of a partially hydrolyzed polyvinyl alcohol. In one more particular embodiment, the polyvinyl alcohol or the co-polymer of the polyvinyl alcohol has a molecular weight range from about 10,000 kDa to about 500,000 kDa and a degree of hydrolysis in the range of about 60% to about 99.9%. In another more particular embodiment, the polyvinyl alcohol has a molecular weight range from about 140,000 kDa to about 500,000 kDa and a degree of hydrolysis in the range of from about 87% to about 99.9%.

In some exemplary embodiments of the aggregarte solid particle, the dispersant is at least one dispersant selected from the group consisting of: sodium lignosulfonate, alkyl naphthalene sulfonate condensate, ethylene oxide/propylene oxide block copolymer, a tristyrylphenol ethoxylates styrene-acrylic copolymer, methylvinylether-maleic anhydride half ester copolymer, and polyvinyl pyrrolidone copolymer.

In some exemplary embodiments, a method of treating a plant is provided. The method includes applying to the surface of a plant or to a surface adjacent to the surface of a plant, an aqueous suspension of a fungicidally effective amount of an aggregate solid particle, wherein said particle is about 1 to about 100 microns in size and wherein said particle includes at least one EBDC fungicide and a matrix or a coating, wherein said matrix or said coating includes at least one EBIS conversion-modulating polymer, comprising at least one polymer selected from the group consisting of: polyvinyl alcohol, latex, gelatin, polyvinylpyrrolidone, polyacrylate, polyacrylamide, polyvinylacetate, polyvinylamine, and polyvinylsulfonate, and wherein the weight ratio of EBIS conversion-modulating polymer to EBDC fungicide weight ratio is from about 1:200 to about 1:5.

In some exemplary embodiments of the method of treating a plant, the EBDC fungicide is mancozeb.

In some exemplary embodiments of the method of treating a plant, the EBDC fungicide produces EBIS on the plant surface upon contact with water and/or oxygen.

In some exemplary embodiments of the method of treating a plant, the polyvinyl alcohol includes at least one polyvinyl alcohol selected from the group consisting of: partially hydrolyzed polyvinyl alcohol, and copolymer thereof.

In some exemplary embodiments of the method of treating a plant, the EBDC fungicide is embedded in a matrix of the EBIS conversion-modulating polymer.

In some exemplary embodiments of the method of treating a plant, the EBDC fungicide is coated with the EBIS conversion-modulating polymer.

In some exemplary embodiments of the method of treating a plant, the aqueous suspension is mixed either in concentrated or dilute form with a non-EBDC fungicide. In a more particular embodiment, the non-EBDC fungicide is effective on diseases caused by oomycete organisms.

In some exemplary embodiments, a method of increasing the efficacy of an EBDC fungicide for preventing or controlling fungal diseases on plant foliage under high humidity conditions is provided. The method includes applying a composition comprising an EBIS conversion-modulating polymer and the EBDC fungicide to at least one surface of plant; and exposing the surface of the plant to air, wherein the air is comprised of about 60% to about 95% relative humidity and at a temperature in the range of about 8 to about 33 degrees C.

In some exemplary embodiments, a method for extending the effective half-life of EBIS conversion from an EBDC fungicide particle is provided. The method includes providing a composition comprising at least one EBDC fungicide and an EBIS conversion-modulating polymer; and contacting said EBDC fungicide and EBIS conversion-modulating polymer composition with water and/or oxygen, wherein the ratio of the residence time of the polymer coated EBDC fungicide is increased by a factor of at least about 1.2 when compared to the uncoated EBDC fungicide as determined by the amount of EBIS produced over time.

BRIEF DESCRIPTION OF THE FIGURES

FIG. 1, a graph, illustrates the EBIS release profiles of various mancozeb formulations in contact with water.

DETAILED DESCRIPTION

Aspects of the present disclosure relate to EBDC fungicides and compositions thereof and their use for controlling or preventing fungal disease or diseases in one or more plants. The described methods comprise contacting a plant at risk of being diseased from a fungal pathogen with a composition comprising an agriculturally effective amount of a ethylene bisdithiocarbamate (EBDC) fungicide, at least one EBIS conversion-modulating polymer, a dispersant, and optionally, other inert formulation ingredients.

In addition, the described compositions may be comprised of at least one EBIS conversion-modulating polymer, at least one EBDC fungicide and, optionally, at least one non-EBDC fungicide.

Unless specifically noted or clearly implied otherwise the term "about" refers to a range of values of plus or minus 10 percent, e.g. about 1 refers to the range 0.9 to 1.1.

While not wishing to be bound by any theory it is believed that dispersing EBDC fungicide molecules, crystals, solid particles and/or aggregate solid particles in a matrix of an EBIS conversion-modulating polymer may beneficially enhance the disease controlling effectiveness of the composition. "Aggregate solid particle" as used herein means a solid particle that is comprised of a number of smaller solid particles and/or crystals that are closely associated or bound with one another. "Dispersing" as used herein means deploying the EBDC fungicide molecules, crystals, solid particles and/or aggregate solid particles with the EBIS conversion-modulating polymer in a homogeneous or heterogeneous and continuous or discontinuous distribution. In the compositions described herein, the EBIS conversion-modulating polymer serves to provide a matrix, a coating, and/or acts as a barrier whereby the rate of reaction of the EBDC fungicide with water and oxygen to produce EBIS, a fungicidally active chemical entity, can be modulated and thereby extend the duration over which fungicidally effective levels of EBIS are present. "Matrix" as used herein means a surrounding material in which another material, including an aggregate solid particle is entrapped, dissolved, dispersed, or otherwise distributed. EBIS conversion modulating polymer may act as a surrounding material in which another material such as an EBDC fungicide is entrapped, dissolved, dispersed or otherwise distributed.

Thus, it is also envisioned that the EBIS conversion-modulating polymer may be present in the matrix at a uniform concentration or as a concentration gradient. EBIS conversion modulating polymer may be deployed as a coating around the EBDC fungicide molecules, crystals, solid particles and/or aggregate solid particles. The compositions described herein may provide improved disease control in spray applications when compared to separately tank-mixing each individual component of the described compositions in the spray mixture and then spraying the mixture on plants.

Suitable EBDC fungicides that can be used in the inventive composition and methods include mancozeb, maneb, zineb and metiram, and more preferably mancozeb. It is envisioned that this disclosure embodies all EBDC fungicides that ultimately produce EBIS. It is also envisioned that the EBDC fungicides of the present disclosure may be complexed and/or coordinated with a broad range of mono- and di-valent cations such as, but not limited to, sodium, copper, manganese, iron, zinc, calcium, magnesium and the like.

Suitable EBIS conversion-modulating polymers in the described compositions are components that modulate the rate of EBIS production from the EBDC fungicide by modulating its reaction with water and oxygen. "Modulate" as used herein, means to reduce the rate of EBIS production when compared to the rate of EBIS production from an EBDC fungicide in the absence of an EBIS conversion-modulating polymer. It is further anticipated that the rate of production and or accumulation of other by-products and metabolites of the EBDC fungicide such as, but not limited to, ethylene bis-isothiocyanate (EBI) and ethylenethiourea (ETU) may also be modulated or reduced by use of an EBIS conversion-modulating polymer.

In one embodiment the EBIS conversion-modulating polymer may serve to provide a homogenous and continuous matrix that allows the EBDC fungicide and inert ingredients to be closely associated with one another. In another embodiment the EBIS conversion-modulating polymer may serve to provide a homogenous and continuous matrix that allows particles of the EBDC fungicide and inert ingredients to be closely associated with one another such that an aggregate particle may be formed. In yet a further embodiment the EBIS conversion-modulating polymer may serve to provide a heterogenous and discontinuous matrix that allows particles of the EBDC fungicide and inert ingredients to closely associate with one another such that an aggregate particle may be formed. In another embodiment the EBIS conversion-modulating polymer may serve as an external coating around the EBDC fungicide particles, dispersants and inerts. In yet another embodiment the EBIS conversion-modulating polymer may be dispersed and distributed uniformly or as a concentration gradient in the EBDC fungicide particles Suitable EBIS conversion-modulating polymers used in the compositions and methods described herein include, but are not limited to, polymers derived from petroleum and natural sources, man-made latexes, gelatins, proteins, polypeptides, peptides, polysaccharides, lignins, gums, celluloses, chitosans, natural latexes, wood rosin and modified derivatives and combinations thereof. Suitable polymers include polyallene, polybutadiene, polyisoprene, and poly (substituted butadienes) such as poly(2-t-butyl-1,3-butadiene), poly(2-chlorobutadiene), poly(2-chloromethyl butadiene), polyphenylacetylene, polyethylene, chlorinated polyethylene, polypropylene, polybutene, polyisobutene, polycyclopentylethylene and polycyclolhexylethylene, polystyrene, poly(alkylstyrene), poly (substituted styrene), poly(biphenyl ethylene), poly(1,3-cyclohexadiene), polycyclopentadiene, polyacrylates including polyalkylacrylates and polyarylacrylates, polyacrylonitriles, polyacrylamides, polymethacrylates, including polyalkylmethacrylates and polyarylmethacrylates, polylactates, polyvinyl pyrrolidones, polydisubstituted esters such as poly(di-n-butylitaconate), and poly(amylfumarate), polyvinylethers such as poly(butoxyethylene) and poly(benzyloxyethylene), poly(methyl isopropenyl ketone), polyvinyl chlorides, polyvinylidene chloride, polyvinyl acetates, polyvinyl alcohols, polyvinyl carboxylate esters such as polyvinyl propionate, polyvinyl butyrate, polyvinyl caprylate, polyvinyl laurate, polyvinyl stearate and polyvinyl benzoate, polyvinylamines, polyvinylsulfonates, polyurethanes, epoxy resins and the like, and modified derivatives, combinations and co-polymers thereof. The EBIS conversion-modulating polymers may be used directly, as solutions in water or as solid or liquid particle dispersions in water.

EBIS conversion-modulating polymers useful in the compositions and methods described herein include polyvinyl alcohols and co-polymers thereof wherein the molecular weight range of the polyvinyl alcohol or co-polymer is from about 10,000 to about 500,000 and the degree of hydrolysis is from about 60% to 99.9%. Preferred polyvinyl alcohols and co-polymers used in the compositions and methods described herein have a molecular weight range from about 140,000 to about 500,000 and a degree of hydrolysis from about 87% to about 99.9%. Suitable commercial polyvinyl alcohols that can be effectively utilized as EBIS conversion-modulating polymers include, for example, Celvol 205 (87-89% degree of hydrolysis, molecular weight <80K), Celvol 540 (87-89% degree of hydrolysis, molecular weight >146K), and Celvol 350 (98-98.8% degree of hydrolysis, molecular weight >146K) Sekisui Chemical Co. Ltd. of Osaka, Japan.

Latexes are generally defined as stable dispersions of polymer microparticles in aqueous medium. Latexes may be natural or synthetic. Latex as found in nature is a milky, sap-like fluid within many plants that coagulates on exposure to air and is a complex emulsion in which proteins, alkaloids, starches, sugars, oils, tannins, resins, and gums are found. Man-made latex is made by polymerizing a monomer or monomers that have been emulsified with surfactants in a water system or by dispersing a powdered polymer in water.

Latexes that are preferred EBIS conversion-modulating polymers in the compositions and methods described herein include standard or modified acrylic latexes, standard or modified vinyl-acrylic latexes, and styrene-acrylic latexes.

The EBIS conversion-modulating polymers in the compositions and methods described herein may comprise, with respect to the total weight of the EBDC fungicide composition, from about 0.1 weight percent (wt %) to about 10 wt %.

It is possible to adjust and further optimize the conversion rates of mancozeb to EBIS or of another pro-pesticide to its active ingredient by adjusting a number of parameters, including: 1) selection of the specific EBIS conversion-modulating polymer, 2) using more than one EBIS conversion-modulating polymers, 3) optimization of the concentration of EBIS conversion-modulating polymer, 4) adjustment of other co-formulants. We also envision use of a combination of wettable powder formulations of EBDC fungicide not containing EBIS conversion-modulating polymer and a composition of EBDC fungicide utilizing a polyvinyl alcohol EBIS conversion-modulating polymer to achieve optimal disease control. While not wishing to be bound by any theory or mechanism, wettable powder formulations of EBDC fungicide not containing EBIS conversion-modulating polymer could offer rapid EBIS generation in the initial application period and extended plant disease control due to prolonged or delayed EBIS production could be achieved by a composition of EBDC fungicide utilizing EBIS conversion-modulating polymer.

The rate of reaction of water and oxygen with EBDC to produce EBIS can be measured and quantified employing methods known to those skilled in the art of reaction analysis. The rate of conversion can be described quantitatively by the EBIS release half-life, $\tau$ (hr), which is the amount of time for one-half of the total theoretical amount of EBIS remaining to be released from the EBDC particle, assuming that all EBDC is ultimately converted to EBIS, or by the EBIS release rate constant, k, wherein $k=\ln 2/\tau$. Depending on the levels and concentrations, EBIS conversion modulating polymers increase the release half-life, $\tau$ (hr) from a factor of about 2 to a factor of about 1000 when compared to the same formulation not containing EBIS conversion modulating polymer. Similarly, depending on the levels and concentrations, EBIS conversion modulating polymers decrease the EBIS release rate constant, k from by a factor of about 1/2 to a factor of about 1/1000 when compared to the same formulation not containing EBIS conversion modulating polymer. The rate of conversion of EBDC fungicide to EBIS can be measured experimentally using analytical methods known to those skilled in the art. The release half-life, $\tau$ (hr) and the release rate constant, k, can be calculated from the analytical measurements using methods and models known to those skilled in the art.

A useful indication of residuality of an EBDC fungicide is the residence time (hrs) (RTH) over which a certain level of EBIS is present after it has been released from EBDC. The RTH can be measured and quantified employing methods known to those skilled in the art of reaction analysis. For example, if 95% of the EBIS was present for an RTH of 70 hr, the residuality might be considered short. As a comparison, extending the RTH beyond 70 hr indicates an improvement (lengthening) of residuality. Depending on the levels and concentrations, EBIS conversion modulating polymers increase the RTH (hr) by a factor of about 1.2 to a factor of about 10 when compared to the same formulation not containing EBIS conversion modulating polymer. As an example, if the RTH of a mancozeb formulation lacking EBIS conversion modulating polymer had a RTH of 50 hr and a comparable mancozeb formulation containing EBIS conversion modulating polymer had a RTH of 125 hr, then the residence time improvement factor would be 2.5 (125 hr/50 hr)

Suitable dispersants used in the compositions and methods described herein may include one or more of a sodium lignosulfonate, an alkyl naphthalene sulfonate condensate, an ethylene oxide/propylene oxide block copolymer, a tristyrylphenol ethoxylates styrene-acrylic copolymer and modifications thereof, a methylvinylether-maleic anhydride half ester copolymer, polyvinyl pyrrolidone, and a poly vinyl pyrrolidone copolymer. The dispersant used in the compositions and methods described herein may comprise, with respect to the total weight of the EBDC fungicide composition, from about 0.1 weight percent (wt %) to about 10 wt %, preferably from about 0.5 wt % to about 5 wt %.

Inert formulation ingredients used in the compositions and methods described herein may include one or more carriers, wetting agents, adjuvants, dispersants, stabilizers, rheology additives, freezing-point depressants, antimicrobial agents, crystallization inhibitors, water and other suitable components known in the art.

The described compositions may be prepared by suitably dispersing in water, in the appropriate particle sizes, the components of the described compositions and then drying the resulting dispersion, for example by spray drying, to provide a dry, wettable powder. The drying may be achieved by spray drying, drum drying or by other methods known to those skilled in the art. The dry, wettable powder may be further processed into other formulation types such as dispersible granules (DG) using known methods.

The described compositions can be used to control diseases caused by fungal pathogens on diverse agricultural and ornamental plants as enumerated in Ladovica, M., et. al. 2010, "Mancozeb Past, Present and Future," *Plant Disease* 94(9) pp 1076-1087, which is expressly incorporated by reference herein.

The effective amount of the described compositions to be employed in controlling or preventing disease development on plants often depends upon, for example, the type of plants, the stage of growth of the plants, severity of environmental conditions, the fungal pathogen and application conditions. Typically, a plant in need of fungal protection, control or elimination is contacted with an effective amount of one or more suitable fungicides diluted in a carrier such as water that will provide from about 1-40,000 ppm, preferably from about 10-20,000 ppm of the one or more fungicides. The contacting may be in any effective manner.

For example, any part of the plant, e.g., foliage, blossoms and stems may be contacted with the composition of the present invention containing EBIS conversion-modulating polymer in mixture with effective rates of an EBDC fungicide and optionally, non-EBDC fungicides. We envision that such compositions could be applied to foliage, blossoms, fruit, and/or stems of plants and that in various instances they could also be effective for improving disease control when applied to seeds, roots and/or tubers or in the general rhizosphere in which the plant is growing.

The compositions described herein may optionally contain one or more non-EBDC fungicides. Such compositions may comprise, with respect to the total weight of the composition, from 10-90 weight percent (wt %) of the one or more non-EBDC fungicides, 1-20 wt % of one or more EBIS conversion-modulating polymers, and 1-90 wt % of one or more inert formulation ingredients such as, for example, one or more dispersants.

Suitable non-EBDC fungicides for use with the described compositions may include copper hydroxide, copper oxychloride, or Bordeaux mixture; phthalimide fungicides such as captan or folpet; amisulbrom; strobilurins such as azoxystrobin, trifloxystrobin, picoxystrobin, kresoxim-methyl, pyraclostrobin, fluoxastrobin, and others; SDHI fungicides such as boscalid, bixafen, fluopyram, isopyrazam, penthiopyrad, fluxapyroxad, benzovindiflupyr, penflufen, sedaxane and others; famoxadone; fenamidone; metalaxyl; mefenoxam; benalaxyl; cymoxanil; propamocarb; dimethomorph; flumorph; mandipropamid; iprovalicarb; benthiavalicarb-isopropyl; valiphenal, valiphenate; zoxamide; ethaboxam; cyazofamid; fluopicolide; fluazinam; chlorothalonil; dithianon; fosetyl-AL, phosphorous acid; tolylfluanid, aminosulfones such as 4-fluorophenyl(1S)-1-({[(1R,S)-(4-cyanophenyl)ethyl]sulfonyl}methyl)-propylcarbamate, oxathiapiprolin, or triazolopyrimidine compounds such as ametoctradin. The non-EBDC fungicides may be mixed into the matrix comprised of the EBDC fungicide and the EBIS conversion-modulating polymer or, alternatively, they can be prepared as diluted spray mixtures by tank-mixing them with the EBDC fungicide and the EBIS conversion-modulating polymer or they may be applied separately in sequential spray applications.

The compositions described herein may be applied to the plant foliage or the soil or area adjacent to the plant. Additionally, the described compositions may be mixed with or applied with any combination of agricultural active ingredients such as herbicides, insecticides, bacteriocides, nematocides, miticides, biocides, termiticides, rodenticides, molluscides, arthropodicides, zoospore attractants, fertilizers, growth regulators and pheromones.

EXAMPLES

Preparation of Representative Compositions

Formulations 1, 2 and 3 (Table 1) were prepared by mixing mancozeb technical grade powder (Dow AgroSciences, Indianapolis, Ind.) with sodium lignosulfonate and Celvol® 540 polyvinyl alcohol (Sekisui Chemical Co. Ltd., Osaka, Japan) solution in water.

The resulting slurry (20-40% solid loading) was then spray dried using a BÜCHI benchtop spray dryer or pilot scale Niro Atomizer to make wettable powders where the mancozeb particles were coated with PVOH. The inlet temperature was controlled at 140 C. and flow rate was 300 mL/h for the benchtop preparation. The inlet temperature was controlled at 160 C. and flow rate was 2~3 L/h for the pilot scale.

TABLE 1

Experimental mancozeb formulations containing EBIS Conversion-modulating polymer.

| Component | Formulation 1 Weight % | Formulation 2 Weight % | Formulation 3 Weight % |
|---|---|---|---|
| Technical grade mancozeb* | 96.2 | 94.7 | 91.8 |
| Celvol 540 polyvinyl alcohol | 0.5 | 2.0 | 5.0 |
| Added sodium lignosulphonate | 3.3 | 3.3 | 3.2 |

*Technical grade contains 80% mancozeb.

The EBIS release profile of Dithane® WP commercial standard and the three formulations listed above were determined in water by preparing a formulation suspension of each. Dithane WP (Dow AgroSciences, Indianapolis, Ind.) contained no EBIS conversion-modulating polymer and served as a control. An equivalent amount of each formulation was weighed and added to 50 ml of MilliQ filtered water, which was previously bubbled with air for 30 minutes to yield a mancozeb suspension concentration of 6.66 mg/mL. Then, an aliquot of 1.5 ml (equivalent to 10 mg mancozeb) was transferred to the interior of a fast-spin dialyzer (1.5 ml chamber from Harvard Apparatus, catalog #74-0505) and the chamber was closed. Finally, the fast-spin dialyzer was placed into an Erlenmeyer flask containing 1 liter of water that was previously bubbled with air for 30 min. The fast-spin dialyzer was under continuous stirring during the whole experiment period. Aliquots of 1 ml were taken over time and transferred to autosampler vials for HPLC analysis of EBIS.

Quantification of EBIS was conducted by an external standardization method, using a freshly prepared EBIS reference standard as the external standard. From EBIS stock standard solution (6500 ng/ml), four working standard solutions were prepared by serial dilutions in water, covering a range of concentrations from 50 to 1625 ng/ml. These four working standards were analyzed by HPLC.

HPLC analysis was performed using an Agilent 1100 HPLC chromatograph system including pump, ultraviolet (UV) detector and auto-sampler; a Phenomenex analytical column Luna C18 4.6×250 mm, 5 um particle size; column temperature 25 C.; mobile phase of water: acetonitrile: methanol (37:30:33 v/v/v); injection volume 5 microliters; flow rate 1.0 ml/min; wavelength: 232 nm and an integrator Agilent EZ Chrom Elite data acquisition system.

As shown in FIG. 1, Dithane® WP (80 wt % mancozeb), the control standard, released EBIS quickly and reached a peak around 170 h, followed by a fast degradation. No EBIS could be detected after 360 h. Formulation 1, containing 0.5% Celvol 540, began EBIS release at about the same time as Dithane® WP. There was no delay in EBIS release but peak EBIS concentrations were not reached until around 270 h. Although Formulation 1 did not reach peak levels of EBIS until about 100 hours later than the control formulation, it also displayed rapid EBIS generation. EBIS could not be detected after ~400 h. Formulations 2 and 3 contained 2% and 5% Celvol 540, respectively, and exhibited much delayed EBIS release. EBIS began to evolve around 120 h. Water and oxygen needs to diffuse through PVA layer to react with mancozeb and EBIS generated needs to diffuse out of PVA layer to be detected and degraded. The balance was well maintained up to 650 h in a plateau. FIG. 1, is a graph that illustrates EBIS release profiles of various mancozeb formulations in water.

The EBIS release half-life $\tau$ (hr) and the EBIS release rate, k, were calculated from the experimental measurements and are shown in Table 2. When compared to a control formulation not containing EBIS conversion-modulating polymer, the test formulations increased the EBIS release half life by a factor of 4 at a EBIS conversion modulating polymer concentration of 0.5%, by a factor of 14 at a EBIS conversion modulating polymer concentration of 2.0%, and by a factor of 39 at a EBIS conversion modulating polymer concentration of 5.0%.

TABLE 2

The EBIS release half-life, $\tau$ and the EBIS release rate, k of Dithane WP and Test Formulations 1, 2 and 3.

| Formulation | PVA % | EBIS release half life[a] $\tau$ (hr) | EBIS release rate constant k = ln2/$\tau$ |
|---|---|---|---|
| Dithane WP | 0 | 21.821 | 0.031765 |
| 1 | 0.5 | 86.31415 | 0.008031 |
| 2 | 2 | 303.9514 | 0.00228 |
| 3 | 5 | 847.936 | 0.000817 |

[a]The amount of time for one-half of the total theoretical amount of EBIS remaining to be released from the EBDC particle, assuming that all EBDC is ultimately converted to EBIS.

As a measure of prolonged EBIS release, the residence time (hr) encompassing 95% release of the theoretical maximum amount of EBIS, was calculated using modeling methods known to those skilled the art. Residence times are shown in Table 3.

TABLE 3

The EBIS Residence Time (hr) of Dithane WP and Formulations 1, 2 and 3.

| Formulation | % PVA | Residence time (hr) encompassing 95% EBIS conversion | Residence time improvement factor |
|---|---|---|---|
| Dithane WP | 0 | 70 | 1 |
| 1 | 0.5 | 110 | 1.6 |
| 2 | 2 | 198 | 2.8 |
| 3 | 5 | 350 | 5 |

The following example with a mancozeb formulation containing a EBIS conversion modulating polymer, Celvol 540 was carried out in greenhouse and growth chamber experiments to evaluate disease control.

Two mancozeb formulations were first exposed to high humidity and then bioassayed with *Pseudoperonospora cubensis* (PSPECU), the causal pathogen of cucumber downy mildew. The mancozeb formulations tested were 1) Dithane WP and 2) Formulation 2 (mancozeb co-formulated with 2% EBIS conversion-modulating polymer'). The formulation Dithane WP contains no EBIS conversion-modulating polymer and thus served as a control.

Cucumbers (*Cucumis sativus* cv Bush Pickle Hybrid #901261) were grown from seed in 5 cm by 5 cm pots containing MetroMix™ growth medium (Scotts, Marysville, Ohio). Plants were raised in greenhouses with supplementary light sources on a 14 hour photoperiod and maintained at 20-26° C. Healthy plant growth was maintained through regular application of dilute liquid fertilizer solution containing a complete range of nutrients. When plants were in the 2-4 true leaf stage of growth, plants with uniform growth were selected for spray application and trimmed to have one true leaf.

Half fold serial dilutions were made in water to form spray solutions with concentrations of 400, 200, 100, 50 and 25 ppm ai. The dilute spray solutions were applied to the surface of the cucumbers with a track sprayer fitted with a Spraying Systems 8003E flat fan nozzle calibrated to deliver 400 L/ha. All treatments were replicated 4 times. A separate tray was used for each combination of rate and formulation type. The sprayed seedlings were separated into groups after the spray application for exposure to the various humidity events and subsequent inoculation with the fungus. After formulations were applied, the plants were allowed to dry and then transferred into a greenhouse and exposed to high humidity for four days. High ambient humidity conditions were created by placing test plants under a translucent plastic hood on a cart in the greenhouse. Water was added to the carts to a depth of about 1 cm to create the high humidity conditions under the hood. Treatments were applied on Day 1 in the morning, allowed to dry, and then exposed in the greenhouse to high humidity until the morning of Day 5 at which time the plants were inoculated. The temperature and humidity were recorded during the test. Temperatures in the greenhouse ranged from 20 C. at night to 30 C. during the day. The relative humidity in carts under the hood ranged from 86-98%. During the day (8:00 am till 8:00 pm) the average relative humidity was 86%, and in the evening (8:00 pm till 8:00 am) the average humidity was 95%.

Following the incubation under high humidity, test plants were then inoculated with sporangia of *Pseudoperonospora cubensis* (PSPECU) at a concentration of 60,000-80,000 sporangia/ml. Inoculated plants were transferred to a dark dew chamber with a temperature of 22 C. After 22 hour in the dew chamber plants were incubated in a lighted growth room with a 14 hour light/dark photoperiod and a temperature of 20 C. Disease development was assessed 5-6 days later when symptoms in untreated check plants were expressed well. Visual assessments of the percent leaf surface infected were made. Results are shown in Table 4 in which % disease as means across rates are presented.

TABLE 4

The effect of extended high humidity on the efficacy of Dithane WP and Formulation 2 on PSPECU four days after inoculation. Data are percent disease.

| Mancozeb Rate ai (ppm) | Dithane WP | Formulation 2 |
|---|---|---|
| 400 | 1 | 1 |
| 200 | 6 | 2 |
| 100 | 27 | 3 |
| 50 | 56 | 21 |
| 25 | 93 | 81 |

While the invention has been described with respect to a limited number of embodiments, the specific features of one embodiment should not be attributed to other embodiments of the invention. No single embodiment is representative of all aspects of the invention. In some embodiments, the compositions or methods may include numerous compounds or steps not mentioned herein. In other embodiments, the compositions or methods do not include, or are substantially free of, any compounds or steps not enumerated herein. Variations and modifications from the described embodiments exist. Finally, any number disclosed herein should be construed to mean approximate, regardless of whether the word "about" or "approximately" is used in describing the number. The appended embodiments and claims intend to cover all those modifications and variations as falling within the scope of the invention.

We claim:

1. An aggregate solid particle comprising:
   an ethylene bisdithiocarbamate (EBDC) fungicide configured to convert to ethylene bis-isothiocyanate sulfide (EBIS), wherein the EBDC fungicide is mancozeb,
   a coating, wherein the coating includes about 2 wt. % to about 10 wt. % of an EBIS conversion-modulating polymer, based on the total weight of the aggregate solid particle, wherein the weight ratio of the EBIS conversion-modulating polymer to the EBDC fungicide is from about 1:100 to about 1:5, and wherein the EBIS conversion-modulating polymer is polyvinyl alcohol; and
   a dispersant.

2. The aggregate solid particle of claim 1, that is from about 1 to about 100 microns in size.

3. A method of treating a plant, comprising the steps of:
   applying to the surface of a plant or to a surface adjacent to the surface of a plant, an aqueous suspension of a fungicidally effective amount of the aggregate solid particle of claim 1.

4. The method of claim 3, further comprising the step of exposing the surface of the plant to air, wherein the air is comprised of about 60% to about 95% relative humidity and at a temperature in the range of about 8 to about 33 degrees C.

5. The aggregate solid particle of claim 1, wherein an EBIS release half-life of the coated EBDC fungicide of the aggregate solid particle is increased by a factor of at least about 2 when compared to an uncoated EBDC fungicide.

6. The aggregate solid particle of claim 1, wherein the EBDC fungicide converts to EBIS when contacted with water and oxygen.

7. The aggregate solid particle of claim 1, wherein the polyvinyl alcohol is selected from a partially hydrolyzed polyvinyl alcohol and a co-polymer of partially hydrolyzed polyvinyl alcohols.

8. The aggregate solid particle of claim 1, wherein the polyvinyl alcohol has a molecular weight range from about 10,000 kDa to about 500,000 kDa and a degree of hydrolysis from 60% to 99.9%.

9. The aggregate solid particle of claim 8, wherein the molecular weight range of the polyvinyl alcohol is from about 140,000 kDa to about 500,000 kDa and the degree of hydrolysis of the polyvinyl alcohol is from 87% to 99.9%.

10. The aggregate solid particle of claim 1, wherein the dispersant is selected from the group consisting of: sodium, calcium or ammonium lignosulfonate, alkyl naphthalene sulfonate condensate, ethylene oxide/propylene oxide block copolymer, tristyrylphenol ethoxylates styrene-acrylic copolymers, methylvinylether-maleic anhydride half ester copolymer, polyvinyl pyrrolidone, and a poly vinyl pyrrolidone copolymer.

11. The aggregate solid particle of claim 1, wherein the aggregate solid particle is produced by a spray drying process.

12. The aggregate solid particle of claim 1, further comprising at least one non-EBDC fungicide.

13. The aggregate solid particle of claim 1, wherein the coating includes about 5 wt. % of the EBIS conversion-modulating polymer, based on the total weight of the aggregate solid particle.

14. The aggregate solid particle of claim 1, comprising about 3 wt. % of the dispersant.

* * * * *